United States Patent
Zhang et al.

(10) Patent No.: US 7,622,416 B2
(45) Date of Patent: Nov. 24, 2009

(54) HYDROGENATION CATALYST, ITS PREPARATION AND USE

(75) Inventors: Chaolin Zhang, Jiangsu (CN); Zheng Chu, Jiangsu (CN); Wei Huang, Jiangsu (CN); Aijun Yang, Jiangsu (CN); Miao Xue, Jiangsu (CN); Hanqiang Jin, Jiangsu (CN)

(73) Assignees: China Petrochemical Corporation, Beijing (CN); Research Institute of Nanjing Chemical Industry Group, Jiangsu (CN)

( * ) Notice: Subject to any disclaimer, the term of this patent is extended or adjusted under 35 U.S.C. 154(b) by 318 days.

(21) Appl. No.: 11/314,943

(22) Filed: Dec. 21, 2005

(65) Prior Publication Data

US 2006/0154810 A1    Jul. 13, 2006

(30) Foreign Application Priority Data

Dec. 24, 2004    (CN) .................. 2004 1 0065880

(51) Int. Cl.
| | |
|---|---|
| *B01J 20/34* | (2006.01) |
| *B01J 38/48* | (2006.01) |
| *B01J 21/18* | (2006.01) |
| *B01J 23/40* | (2006.01) |
| *B01J 23/74* | (2006.01) |
| *C07C 51/42* | (2006.01) |

(52) U.S. Cl. ................... 502/185; 502/22; 562/485
(58) Field of Classification Search ............ 502/22, 502/185
See application file for complete search history.

(56) References Cited

U.S. PATENT DOCUMENTS

| | | | |
|---|---|---|---|
| 3,737,395 A | 6/1973 | Arnold et al. | |
| 4,394,299 A | 7/1983 | Puskas et al. | |
| 4,415,479 A | 11/1983 | Puskas et al. | |
| 4,421,676 A | 12/1983 | Puskas et al. | |
| 4,467,110 A | 8/1984 | Puskas et al. | |
| 4,476,242 A | 10/1984 | Puskas et al. | |
| 4,728,630 A | 3/1988 | Schroeder et al. | |
| 4,791,226 A | 12/1988 | Puskas et al. | |
| 4,892,972 A * | 1/1990 | Schroeder et al. | ............ 562/487 |
| 5,302,183 A * | 4/1994 | De Boer et al. | ............ 75/426 |
| 5,449,655 A * | 9/1995 | Albers et al. | ............ 502/185 |
| 6,066,589 A | 5/2000 | Malentacchi et al. | |
| 6,753,290 B1 * | 6/2004 | Romanenko et al. | ........ 502/185 |

(Continued)

FOREIGN PATENT DOCUMENTS

CN    1283521    2/2001

(Continued)

OTHER PUBLICATIONS

Partial English Translation of CN 1457922 dated Nov. 26, 2003.

(Continued)

*Primary Examiner*—Patricia L Hailey
(74) *Attorney, Agent, or Firm*—Ladas & Parry LLP

(57) ABSTRACT

The present invention discloses a hydrogenation catalyst comprising metallic palladium supported on activated carbon support, wherein the penetration depth of metallic palladium in the support is at least about 10 μm and up to about 100 μm, the crystallite size of palladium is between about 40 Å and about 120 Å, and the palladium in the surface layer from the surface of support to a depth of 1 μm is from about 5% to about 40% based on the total atom number of palladium and other elements. The present invention further discloses a process for preparing the hydrogenation catalyst, and a use of said hydrogenation catalyst in the purification of crude terephthalic acid.

19 Claims, 1 Drawing Sheet

U.S. PATENT DOCUMENTS 7,041,847 B2 * 5/2006 Haake et al. ................ 562/487

FOREIGN PATENT DOCUMENTS

| CN | 1436595 | 8/2003 |
|---|---|---|
| CN | 1457922 | 11/2003 |

OTHER PUBLICATIONS

Partial English Translation of CN 1436595 dated Aug. 20, 2003.
Partial English Translation of CN 1283521 dated Feb. 14, 2001.

* cited by examiner

HYDROGENATION CATALYST, ITS PREPARATION AND USE

TECHNICAL FIELD

The present invention belongs to catalytic technical field and relates to a hydrogenation catalyst, its preparation and use. Specifically, the present invention relates to a hydrogenation catalyst comprising metallic palladium supported on activated carbon support and its preparation, and said hydrogenation catalyst is used in particular in purification of crude terephthalic acid.

BACKGROUND ART

It is well known that terephthalic acid is suitable for the production of polyester and copolymer thereof in textile fibre, and this polymer and copolymer thereof can be made by condensation of terephthalic acid and dihydric alcohol. Crude terephthalic acid can be purified by hydrogenation in the presence of a suitable catalyst, and hydrogenation is the easiest route for removal of 4-carboxylbenzaldehyde (4-CBA) impurity from the crude terephthalic acid.

Catalyst comprising a Group VIII metal of the Periodic Table of Elements supported on an inert support is useable in various hydrogenation reactions. Such a catalyst is typically prepared by impregnating a support material with a solution of a compound of Group VIII metal and then reducing the impregnated compound to the metal. Similar to other supported catalysts, the activity and selectivity of a catalyst comprising a Group VIII metal supported on a support depend on many factors, such as the amount of active metal component supported on the support, the type of support, and the process for preparing the catalyst, i.e., the process for depositing or dispersing the Group VIII metal on the support.

Pa/C catalyst is a common hydrogenation catalyst, and its studies and improvements always focus on the distribution state of metallic palladium as active component on support, because this greatly affects the property of catalyst.

As to a catalyst comprising a noble metal as active component supported on a granular or shaped activated carbon support, the active component is generally distributed on the surface of support, and the active component distributed in the support is out of function. Initially, the active component is distributed deeply in support, for example, U.S. Pat. No. 4,791,226 discloses the distribution of palladium is within a range of 0-500 µm from the surface of support. U.S. Pat. No. 4,728,630 mentions that metal crystallites are mainly distributed in a range from the surface of support to a depth of at least about 5 µm, and said depth is preferably from about 10 to 20 µm. U.S. Pat. No. 4,467,110 mentions that the penetration depth of active component in a porous support ranges from about 70 to about 150 µm from the surface of support. CN1,283,521A mentions that the active component of catalyst is distributed in a layer from the outer surface of support to a depth of 1%-30% of the radius thereof. U.S. Pat. No. 6,066,589 mentions that less than 50 wt % of palladium is comprised in a surface layer having a thickness of up to 50 µm, and the remainder is distributed in an inner layer having a depth from about 50 to about 400 µm. These studies about the distribution of palladium active component in support indicate that the property of catalyst is improved in some extent.

As to the crystallite size of metallic palladium active component, the main common understanding in the recent studies is that the smaller the better, i.e., the crystallite size is less than 35 Å, and the smaller crystallite size, the more uniform distribution of metallic palladium active component on support. For example, U.S. Pat. Nos. 4,415,479, 4,421,676 and 4,791,226 all mention that the palladium crystallite size in catalyst are less than 35 Å. U.S. Pat. No. 4,394,299 and U.S. Pat. No. 4,791,226 further teach that when the palladium crystallite size in catalyst are greater than 35 Å, the surface area of palladium decreases, and the activity of Pd/C catalyst in the hydrogenation of 4-CBA decreases as well.

In the meantime, it is by no means that the higher the palladium content on the surface of support is the better, because when a large amount of metallic palladium concentrates on the surface of support, the formation of palladium cluster will be facilitated and the crystallite size of metallic palladium will increase, which causes the decrease of the surface area of palladium and the decrease of catalytic activity. Further, when a large amount of metallic palladium concentrates on the surface of support, the loss of metallic palladium caused by the erosion of stuffs will increase during the hydrogenation of terephthalic acid. If the palladium content on the surface of support is at a relatively low level, the surface area of palladium and the catalytic activity will decrease as well. Thus, it is very important to control the palladium content on the surface of support.

Currently, as to a process for preparing a catalyst comprising a Group VIII metal supported on an activated carbon support, reports mainly focus on the following aspects: (1) mixing by a mechanical stirrer, for example, U.S. Pat. Nos. 4,791,226, 4,415,479, 4,394,299, 4,421,676, etc. all stir with a paddle, located in a solvent layer above the carbon in order to uniformly adsorb a palladium salt solution on an activated carbon support; and (2) mixing by a rotating reactor, for example, U.S. Pat. No. 4,728,630, CN1,283,521A, etc. use a cylindrical vessel to uniformly mix a palladium salt solution and an activated carbon support. Both of these two manners can uniformly mix solution and support.

The mechanical stirrer is generally suitable for a noble metal catalyst supported on a powdery carbon support. As to a granular or shaped carbon support, when the amount of support is at a relatively low level, the support can readily contact with solution sufficiently and is hardly broken by the stirrer, but when the amount of support is at a relatively high level, the support cannot sufficiently contact with solution under mechanical stirring. Under gentle stirring condition, there are some corners without stirring, where the support is actually impregnated with solution under static state; further, the activated carbon support generally is basic, and such a strong basic will facilitate the formation of noble metal hydroxide deposit, which will cause the loss of noble metal. Under vigorous stirring condition, although there is no corner without stirring, the light activated carbon moves with the eddy caused by the stirring and is damaged extremely by the stirrer. In particular, as to the hydrogenation catalyst for purifying terephthalic acid, the metallic palladium in shell distribution on the surface of support may be brushed off by the vigorous stirring, so that the obtained catalyst may have a reduced surface palladium content and a reduced activity.

The rotating reactor generally employs a non-excessive adsorption technique, i.e., the quantity of the adsorbed solution is not more than the saturated adsorption capacity of support. With the use of such a technique, said reactor generally is suitable for preparing a catalyst comprising an active component distributed on the surface of support, such as a Pd/C catalyst for the hydrogenation and purification of terephthalic acid. Said reactor uses a nozzle to atomize the solution, and the support rotates with the reactor in order to form uniform adsorption. However, it is difficult to sufficiently contact the rotating activated carbon support with the atomized solution, which facilitates the formation of nonuniform adsorption. Further, due to the non-excessive adsorption of the activated carbon, the directly friction among particles of activated carbon will cause the formation of fine powder of catalyst and the loss of noble metal.

It can be seen that people still want to develop a catalyst comprising a distinct metallic palladium distribution on a support, and a corresponding process for preparing said catalyst via continuous studying.

SUMMARY OF THE INVENTION

The present invention mainly relates to a catalyst with excellent performance prepared by using a fluidized bed, wherein said fluidized bed enables to deposit uniformly metallic palladium on the surface of granular or shaped activated carbon support. The inventors surprisingly discovered that the obtained catalyst possesses a distinct distribution of metallic palladium, has a higher activity and/or selectivity for reducing 4-CBA during hydrogenating 4-CBA to 4-methylbenzoic acid, and has a longer service life.

Specifically, one object of the present invention is to provide a hydrogenation catalyst comprising metallic palladium supported on activated carbon support, wherein the penetration depth of metallic palladium in the support is at least about 10 μm and up to about 100 μm, the crystallite size of palladium in the surface layer is between about 40 Å and about 120 Å, and the palladium is present in the surface layer from the surface of the support to a depth of 1 μm in an atom number that is from about 5% to 40% of the total atom number of palladium and other elements in this surface layer.

Another object of the present invention is to provide a process for preparing said hydrogenation catalyst, which is carried out by using a fluidized bed. Said process comprises placing activated carbon support between two sieve plates in the fluidized bed, circularly passing upward an aqueous solution through the fluidized bed by using a pump under conditions of effectively fluidizing the activated carbon support, then adding a solution of palladium salt under fluidizing state for impregnating the activated carbon support.

Another object of the present invention is to provide a process for purifying crude terephthalic acid by using said hydrogenation catalyst, wherein said crude terephthalic acid is generated by the oxidation reaction of p-xylene and contains 4-CBA impurity.

DETAILED DESCRIPTION OF THE INVENTION

The technical solution of the present invention is described in detail hereinafter.

The hydrogenation catalyst of the present invention comprises metallic palladium supported on activated carbon support, wherein the penetration depth of metallic palladium in support is at least about 10 μm and up to about 100 μm, the crystallite size of palladium is between about 40 Å and about 120 Å, and the palladium in the surface layer from the surface of support to a depth of 1 μm is from about 5% to about 40% based on the total atom number of palladium and other elements. During the purification of crude terephthalic acid, it is confirmed that the catalyst of the present invention is effective and can reduce the content of 4-CBA to a relatively low level.

In a preferred embodiment of the hydrogenation catalyst of the present invention, the penetration depth of metallic palladium in support is at least about 15 μm and up to about 100 μm, the crystallite size of palladium is between about 40 Å and about 80 Å, and the palladium in the surface layer from the surface of support to a depth of 1 μm is from about 10% to about 30% based on the total atom number of palladium and other elements.

The activated carbon support for supporting metallic active component in the present invention can be of animal origin or plant origin. Coconut carbon is preferred. The surface area of the activated carbon support is preferably greater than 600 $m^2/g$ (BET) and can reach 1000 $m^2/g$; the porosity is 0.3-0.9 ml/g. In the present invention, it preferably uses activated carbon support in a granular form; however, it is possible to use activated carbon support in the form of sphere, cylinder or other specific shapes.

The pretreatment of activated carbon support is the first step for preparing the catalyst, which is performed generally by a manner of acid washing with an acidified aqueous solution, mainly to reduce the ash content of activated carbon and to adjust the structure of functional groups on the surface of activated carbon support, wherein the used acid can be hydrochloric acid, nitric acid, phosphoric acid, and the like. Optionally, the activated carbon support may be further treated by adding oxidant, such as hydrogen peroxide, sodium hypochlorite. Examples of these pretreatment method are found in CN1,457,922A, CN1,436,591A and U.S. Pat. No. 6,066,589, the descriptions of each being incorporated herein by reference in entirety.

In the present invention, the amount of metallic palladium supported on activated carbon support is from about 0.1 to about 5 wt % based on the total weight of catalyst; preferably, in the case of catalysts for purifying crude terephthalic acid, from about 0.2 to about 0.6 wt %; more preferably, from about 0.3 to about 0.5 wt %. In addition to palladium, other Group VIII metals of the Periodic Table of Elements, such as ruthenium, platinum, rhodium, iridium, may be present in the catalyst.

The active component of the catalyst is derived from salt compounds thereof. The examples of selectable palladium salts are palladium halides, palladium nitrate, palladium acetate, chloropalladium acid, etc., and the commonly used is palladium chloride or palladium nitrate.

The present invention provides a process for preparing a carbon-supported hydrogenation catalyst by using a fluidized bed, wherein the circulation of aqueous solution drives the motion of granular activated carbon support. Since the circulation of aqueous solution for driving the motion of catalyst is more gentle than conventional mechanical stirring or cylinder rotating, the support contacts with the aqueous solution more sufficiently, the noble metal component is deposited on the surface of activated carbon support more uniformly, the loss of noble metal caused by the formation of fine powder under mechanical stirring or cylinder rotating is avoided, and the more economic benefit is obtained.

In one embodiment of the present invention, the activated carbon support is placed inside a fluidized bed, and an amount of water is added. A pump is used so that the motion of activated carbon support in the fluidized bed is driven by aqueous solution. Then, a palladium salt impregnating solution is added. Since the support contacts with the impregnating solution sufficiently, palladium is adsorbed on the support uniformly. According to the conventional process in the art, for example U.S. Pat. Nos. 3,737,395, 2,857,337 and CN1, 436,595A incorporated herein by reference in entirety, a precipitating agent is added to deposit the palladium, and finally the obtained mixture is treated with reducing agent of a known kind, such as formaldehyde, hydrazine, glucose, glycerin, and the like, for reducing palladium to metallic palladium. A catalyst is obtained by further washing and drying steps.

In another embodiment of the present invention, the palladium salt impregnating solution is firstly treated with an oxidant to form a palladium salt oxidation solution, then said palladium salt oxidation solution is added to the fluidized bed to impregnate the activated carbon support. In the present invention, the used oxidant is hydrogen peroxide, sodium hypochlorite or a mixture thereof, having a concentration of from about 0.01% to about 10%. Preferably, an aqueous solution of a mixture of hydrogen peroxide and sodium hypochlorite having a mass ratio of from 1-30:1 is used.

As to the process of the present invention, the palladium impregnating solution contacts with the support at room temperature or above, preferably a temperature ranging from about 15 to about 60° C. The precipitating agent is preferably subcarbonates, dicarbonates or alkaline earth metal hydroxides.

The fluidized bed used in the process of the present invention is equipped with sieve plates at its upper and lower portions. One effect of said sieve plates is to prevent the catalyst from entering into pump, so that the catalyst is not broken by the blades in pump, and the loss of noble metal is avoided. Another effect of said sieve plates is to help to maintain uniform motion of support in the fluidized bed, so that the support can effectively contact with the solution of noble metal sufficiently. The preferably used sieve plates have a orifice diameter of 1-3 mm and a orifice pitch of 2-6 mm.

In the process of the present invention, the activated carbon support is charged between two sieve plates in the fluidized bed, the impregnating solution is pumped to pass upward through sieve plate at the lower portion, activated carbon bed, sieve plate at the upper portion of the fluidized bed, and a discharging pipe at the upper side of the fluidized bed, and then enters into the circulation in pump. The activated carbon support between the two sieve plates contacts with the impregnating solution sufficiently, so that the active component of catalyst deposits on the outer surface of the activated carbon support uniformly, and then enters into the inner part of support to form a distinctive penetration depth.

The thickness of palladium distributed on the support is controlled by regulating the flow rate of solution, and the flow rate of solution is preferably controlled between about 3.0 and about 35.0 L/min. As compared to the prior art, the catalyst of the present invention has a penetration depth of metallic palladium active component in support of at least about 10 μm and up to about 100 μm, preferably of at least about 15 μm and up to about 100 μm, i.e., the active component is neither totally on the outer surface, nor largely distributed in the inner part of support. If the active metallic palladium is totally distributed on the outer surface, the metallic palladium may be brushed off by stuffs during the reaction, so that the catalytic activity is reduced; further, the concentration of a large quantity of metallic palladium on the outer surface may facilitate the formation of palladium clusters, increase the crystallite size of palladium, reduce the surface area of palladium, the activity and service life of catalyst. However, if the metallic palladium is largely distributed in the inner part of support, the surface palladium content will decrease, and a large quantity of metallic palladium cannot be utilized. Moreover, it is practically confirmed that metallic palladium diffuses toward the surface in the used catalyst. Thus, it is very important to maintain a reasonable metallic palladium penetration depth. The catalyst prepared according to the process of the present invention has a longer service life.

The crystallite size of metallic palladium also affects the hydrogenation activity of catalyst. A relatively large crystallite size, i.e., greater than 120 Å, may facilitate the formation of metallic palladium clusters, and then results in lower surface area of palladium and in lower activity of catalyst. Usually, the used catalyst has a crystallite size of metallic palladium of greater than 120 Å. However, if the metallic palladium in catalyst has a relatively small crystallite size, i.e., less than 35 Å, many palladium crystallites may enter into the inner part of support, which results in the decrease of surface palladium content and the decrease of surface area of palladium. Moreover, a large amount of crystallites may cause the sintering phenomena of the active component in catalyst during the reaction. In particular, as to a catalyst for the hydrogenation purifying of terephthalic acid, since the hydrogenation reaction of 4-CBA is an exothermic reaction, if the reaction heat cannot be released in time, it will cause the sintering phenomena, so that the crystallite size of palladium in catalyst increases and the activity of catalyst decreases. Thus, an appropriate crystallite size of palladium is also very important. The process of the present invention can obtain the uniform distribution of metallic palladium active component on the surface of support in order to increase the surface area of palladium, and the distribution of metallic palladium in the inner part of support in some extent in order to increase the penetration depth of metallic palladium in support. The appropriate crystallite size of metallic palladium is from about 40 Å to about 120 Å, in particular from about 40 Å to about 80 Å.

In addition, the process of the present invention can control well the atom number of palladium as active component in the surface layer of activated carbon support. Specifically, the palladium in the surface layer from the surface of support to a depth of 1 μm is from about 5% to about 40%, preferably from about 10% to about 30% based on the total atom number of palladium and other elements. Such a palladium atom number distribution may facilitate the increase of catalytic activity.

Another advantage of using the fluidized bed for preparing a carbon-supported noble metal catalyst lies in that the steps of impregnation, deposition, reduction and washing can be carried out in the same one fluidized bed. Thus, the process of the invention has merits of simple flow path, easy operation, short production period and convenient for production in large scale. Since support particles move uniformly in the fluidized bed, noble metal can be distributed on support more uniformly in comparison with the conventional batch reactor, and the catalyst has higher catalytic activity. Secondly, heat is distributed in the fluidized bed uniformly, and the uniformity of heat distribution is more advantageous for preparing catalyst needed heat treatment. Thirdly, during the step of washing catalyst, the fluidized bed has characteristics of clean washing and small water consumption. Fourthly, the fluidized bed facilitates the drying of catalyst and reduces the fuel consumption. Thus, the use of fluidized bed for preparing catalyst is especially suitable for preparing a catalyst comprising noble metal active component distributed on the surface of granular support.

In the present invention, the distribution of palladium is measured by LEO-1530VP scanning electron microscope. The crystallite size of palladium is determined by X-fluorescence spectrometer and X-ray diffractometer (XRD).

The evaluation of catalytic activity: loading 0.5 g catalyst into a 0.5 L autoclave, adding stainless steel screen meshes to prevent the catalyst from being broken by contacting with stirrer, adding 30 g crude terephthalic acid (TA), adding 4-CBA so that the 4-CBA content reaches 8000 ppm/g TA, 270 ml water, 0.3 MPa $H_2$, reacting at 280° C. for 1 hour, and representing the catalytic activity with 4-CBAg/gCat.h (the amount of 4-CBA treated by per gram of catalyst per hour, wherein the amount of the treated 4-CBA is the difference between the amount of the added 4-CBA and the amount of the residual 4-CBA), wherein the amount of 4-CBA is determined by high performance liquid chromatography assay.

In general, the activity of catalyst is represented by the conversion rate of 4-CBA (for example, CN1,457,922A), but this rate depends greatly on the amount of catalyst and reaction time, while this problem is solved by representing the catalytic activity by 4-CBAg/gCat.h (the amount of 4-CBA treated by per gram of catalyst per hour), so that the testing results are more objective and comparable.

The Table 1 lists the activity data of catalysts as disclosed by the documents in the prior art, which are represented by 4-CBAg/gCat.h according to the foregoing method for activity evaluation. Take U.S. Pat. No. 4,421,676 for example, the method for activity evaluation comprises: adding 4-CBA to 12.9 g crude terephthalic acid (TA) so that the 4-CBA content reaches 7900 ppm/gTA, adding 150 ml water, 0.17 g catalyst, reacting for 3.75 hours, wherein the minimum 4-CBA content after the end of reaction is 39 ppm/gTA. The activity 4-CBAg/gCat.h=$(7900-39) \times 10^{-6} \times 12.9/(0.17 \times 3.75)=0.159$ via calculation.

TABLE 1

| | Activities of catalysts (4-CBAg/gCat · h) | | | | |
|---|---|---|---|---|---|
| Documents | CN1,283,521 | US4,421,676 | US4,467,110 | US4,791,226 | CN14,579,22A |
| (4-CBAg/gCat · h) | 0.202 | 0.159 | 0.181 | 0.171 | 0.265 |

The catalyst prepared according to the process of the present invention has a catalytic activity of greater than 0.4 g 4-CBA/gCat.h, which is far better than that of the catalysts in the prior art.

The catalytic activity may also be represented by the ratio of the slope of straight line obtained by plotting the logarithm of the concentration of 4-CBA as a function of the reaction time in minute to the palladium weight in gram. For example, U.S. Pat. No. 6,066,589 discloses such ratio of between 10 and 20. The catalyst prepared according to the process of the present invention has such ratio of greater than 20, i.e., its activity is higher than that of the catalyst of U.S. Pat. No. 6,066,589.

EXAMPLES

Figure 1:
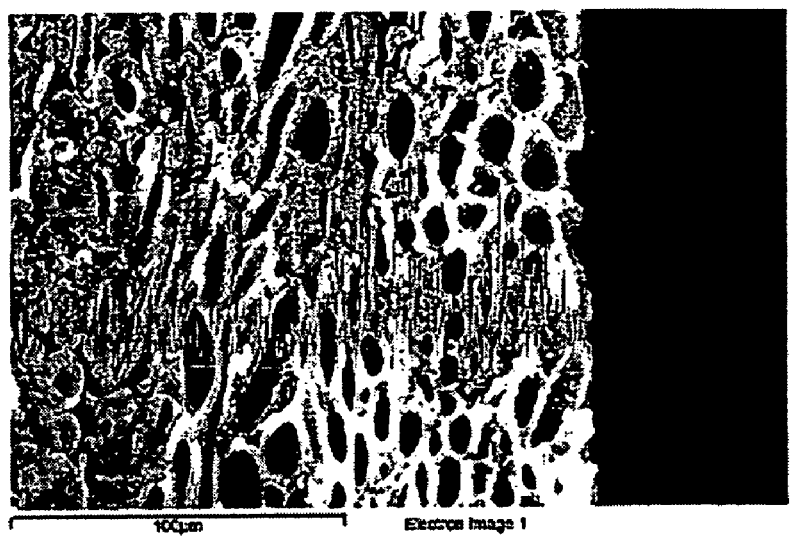
FIG. 1 is the scanning electron microscope picture of the section of catalyst G of Example 7 of the present invention, wherein LEO-1530VP scanning electron microscope is used to observe the penetration depth of palladium, the white color in the picture represents the distribution of metallic palladium, and the penetration depth is within 100 μm.
Figure 2:
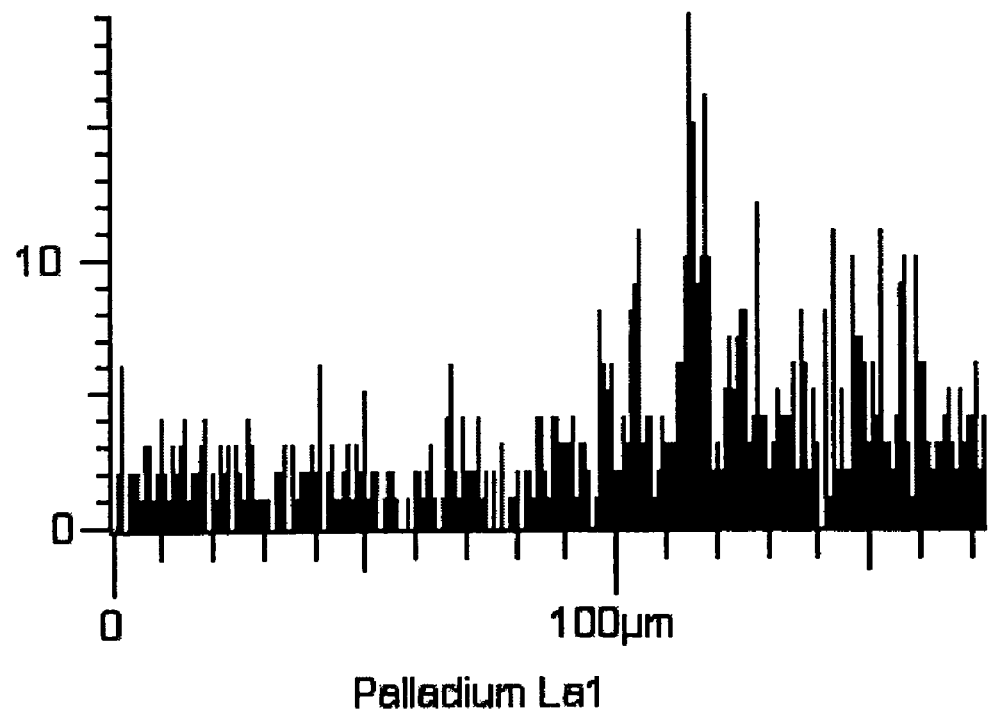
FIG. 2 is the palladium distribution scanning electron microscope picture of the section of catalyst G of Example 7 of the present invention, wherein the ordinate represents approximate palladium concentration, and the abscissa represents palladium penetration depth.

The following examples are presented to further illustrate the details and advantages of the present invention, but not to limit the protection scope of the invention. The protection scope of the invention is defined by the appended claims.

The pre-treatment of support: 500 g activated coconut carbon having a size of 4-8 mesh is heat-treated with 2000 ml 10% hydrochloric acid aqueous solution at 50° C. for 2 hours, then filtered and washed with deionized water until no chlorine ion is datable by silver nitrate solution, and filtered again to obtain the pre-treated activated coconut carbon.

The process for preparing catalyst: a pretreated activated carbon support is used, which adsorbs a palladium salt oxidization solution in a fluidized bed until the solution becomes colorless; a subcarbonate or a bicarbonate or an alkaline earth metal hydroxide is added to deposit palladium; then formaldehyde, hydrazine hydrate, glucose or hydrogen is added for reduction; and a catalyst product is finally obtained by washing and drying.

The fluidized bed used for preparing the catalyst of the present invention: having a diameter of 100 mm, a bed height of 400 mm, a nozzle diameter of 10 mm, a sieve orifice diameter of 2 mm, and a orifice pitch of 4 mm.

Palladium salt oxidization solution: 4.237 g $PdCl_2$, 20 ml 37% hydrochloric acid aqueous solution, 150 ml hydrogen peroxide, 30 ml sodium hypochlorite, and 800 ml deionized water are added to a 2000 ml beaker and are formulated to obtain 1000 ml palladium salt oxidation solution.

Example 1

Catalyst A 500 g of the pretreated activated coconut carbon with a size of 4-8 mesh were weighed, rinsed with water to remove carbon fines, and then placed in a 5000 ml four-necked flask. 2000 ml water was added, stirred by a stirrer under aqueous solution and above carbon layer. 1000 ml of the palladium salt oxidization solution as above formulated was added and was adsorbed at room temperature under stirring until the impregnating solution was colorless. Under stirring, 500 ml of 5% $Na_2CO_3$ aqueous solution was added and maintained for 2 hours at room temperature, and then 500 ml of formaldehyde was added to perform the reduction reaction at room temperature or slightly above for 4 hours, following by filtering, washing with deionized water until no chlorine ion was datable. The catalyst was discharged from the flask, and dried at 110° C. for 5 hours.

Example 2

Catalyst B 500 g of pretreated activated coconut carbon with a size of 4-8 mesh were weighed, rinsed with water to remove carbon fines, and placed in the fluidized bed. 5000 ml water was added, and circulated at a flow rate of 1.2 L/min by using a pump, wherein the activated carbon was immobilized as a fixed bed for adsorption. Then, 1000 ml of the palladium salt oxidization solution as above formulated was added and the impregnation was performed at room temperature until the impregnating solution was colorless. Under stirring, 500 ml of 5% $Na_2CO_3$ aqueous solution was added and maintained for 2 hours at room temperature, and then 500 ml of formaldehyde was added to perform the reduction reaction at room temperature or slightly above for 4 hours, following by filtering, washing with deionized water until no chlorine ion was datable. The catalyst was discharged from the fluidized bed, and dried at 110° C. for 5 hours.

Example 3

Catalyst C 500 g of pretreated activated coconut carbon with a size of 4-8 mesh were weighed, rinsed with water to remove carbon fines, and placed in the fluidized bed. 5000 ml water was added, and circulated at a flow rate of 3.0 L/min by using a pump, wherein the activated carbon was slightly moved as a fixed-fluidized bed for adsorption. Then, 1000 ml of the palladium salt oxidization solution as above formulated was added and the impregnation was performed at room temperature until the impregnating solution was colorless. Under stirring, 500 ml of 5% $Na_2CO_3$ aqueous solution was added and maintained for 2 hours at room temperature, and then 500 ml of formaldehyde was added to perform the reduction reaction at room temperature or slightly above for 4 hours, following by filtering, washing with deionized water until no chlorine ion was datable. The catalyst was discharged from the fluidized bed, and dried at 110° C. for 5 hours.

Example 4

Catalyst D 500 g of pretreated activated coconut carbon with a size of 4-8 mesh were weighed, rinsed with water to remove carbon fines, and placed in the fluidized bed. 5000 ml water was added, and circulated at a flow rate of 6.0 L/min by using a pump, wherein the activated carbon was crept as a fixed-fluidized bed for adsorption. Then, 1000 ml of the palladium salt oxidization solution as above formulated was added and the impregnation was performed at room temperature until the impregnating solution was colorless. Under stirring, 500 ml of 5% $Na_2CO_3$ aqueous solution was added and maintained for 2 hours at room temperature, and then 500 ml of formaldehyde was added to perform the reduction reaction at room temperature or slightly above for 4 hours, following by filtering, washing with deionized water until no chlorine ion was datable. The catalyst was discharged from the fluidized bed, and dried at 110° C. for 5 hours.

Example 5

Catalyst E 500 g of pretreated activated coconut carbon with a size of 4-8 mesh were weighed, rinsed with water to remove carbon fines, and placed in the fluidized bed. 5000 ml water was added, and circulated at a flow rate of 9.0 L/min by using a pump, wherein the activated carbon was fluidized as a fluidized bed for adsorption. Then, 1000 ml of the palladium salt oxidization solution as above formulated was added and the impregnation was performed at room temperature until the impregnating solution was colorless. Under stirring, 500 ml of 5% $Na_2CO_3$ aqueous solution was added and maintained for 2 hours at room temperature, and then 500 ml of formaldehyde was added to perform the reduction reaction at room temperature or slightly above for 4 hours, following by filtering, washing with deionized water until no chlorine ion was datable. The catalyst was discharged from the fluidized bed, and dried at 110° C. for 5 hours.

Example 6

Catalyst F 500 g of pretreated activated coconut carbon with a size of 4-8 mesh were weighed, rinsed with water to remove carbon fines, and placed in the fluidized bed. 5000 ml water was added, and circulated at a flow rate of 24 L/min by using a pump, wherein the activated carbon was fluidized to fill ⅔ volume of bed as a fluidized bed for adsorption. Then, 1000 ml of the palladium salt oxidization solution as above formulated was added and the impregnation was performed at room temperature until the impregnating solution was colorless. Under stirring, 500 ml of 5% $Na_2CO_3$ aqueous solution was added and maintained for 2 hours at room temperature, and then 500 ml of formaldehyde was added to perform the reduction reaction at room temperature or slightly above for 4 hours, following by filtering, washing with deionized water until no chlorine ion was datable. The catalyst was discharged from the fluidized bed, and dried at 110° C. for 5 hours.

Example 7

Catalyst G 500 g of pretreated activated coconut carbon with a size of 4-8 mesh were weighed, rinsed with water to remove carbon fines, and placed in the fluidized bed. 5000 ml water was added, and circulated at a flow rate of 30 L/min by using a pump, wherein the activated carbon was fluidized to fill the whole bed as a fluidized bed for adsorption. Then, 1000 ml of the palladium salt oxidization solution as above formulated was added and the impregnation was performed at room temperature until the impregnating solution was colorless. Under stirring, 500 ml of 5% $Na_2CO_3$ aqueous solution was added and maintained for 2 hours at room temperature, and then 500 ml of formaldehyde was added to perform the reduction reaction at room temperature or slightly above for 4 hours, following by filtering, washing with deionized water until no chlorine ion was datable. The catalyst was discharged from the fluidized bed, and dried at 110° C. for 5 hours.

Example 8

Catalyst H 500 g of pretreated activated coconut carbon with a size of 4-8 mesh were weighed, rinsed with water to remove carbon fines, and placed in the fluidized bed. 5000 ml water was added, and circulated at a flow rate of 40 L/min by using a pump, wherein the activated carbon was compressed to the upper sieve plate in the fluidized bed as a fixed bed for adsorption. Then, 1000 ml of the palladium salt oxidization solution as above formulated was added and the impregnation was performed at room temperature until the impregnating solution was colorless. Under stirring, 500 ml of 5% $Na_2CO_3$ aqueous solution was added and maintained for 2 hours at room temperature, and then 500 ml of formaldehyde was added to perform the reduction reaction at room temperature or slightly above for 4 hours, following by filtering, washing with deionized water until no chlorine ion was datable. The catalyst was discharged from the fluidized bed, and dried at 110° C. for 5 hours.

The results are shown in Table 2.

TABLE 2

| Catalyst | Pd content (wt %) | Pd content in ≦1 μm surface layer (%)[1] | Crystallite size (Å)[2] | Penetration depth of palladium in support (μm) | Activity (4-CBAg/gCat · h) | Conversion rate of 4-CBA (%) |
|---|---|---|---|---|---|---|
| A | 0.35 | 42.87 | 83 | 5 | 0.443 | 92.3 |
| B | 0.38 | 28.08 | 127 | 10 | 0.432 | 90.0 |
| C | 0.39 | 27.86 | 110 | 10 | 0.453 | 94.4 |
| D | 0.44 | 24.89 | 75 | 15 | 0.465 | 96.8 |
| E | 0.46 | 24.08 | 69 | 25 | 0.467 | 97.2 |
| F | 0.47 | 17.92 | 48 | 50 | 0.468 | 97.6 |
| G | 0.48 | 11.48 | 47 | 100 | 0.471 | 98.2 |
| H | 0.39 | 4.82 | ☐35 | 200 | 0.406 | 84.6 |

Annotation:
[1] Pd content in ≦1 μm surface layer was the percentage of Pd based on the total atom number of Pd and other elements in the layer from the outer surface to a depth about 1 μm, which was measured by LEO-1530VP scanning electron microscope;
[2] the crystallite size of palladium was measured by X-fluorescence spectrometer and X-ray diffractometer (XRD).

According to the data in Table 2, the catalyst of the present invention has good catalytic activity; when a carbon-supported noble metal catalyst is prepared by using a fluidized bed, by adjusting the flow rate of solution, the flow state of support in the solution can be regulated, and the distribution of noble metal active component on support can be regulated thereby; preferably, the penetration depth of metallic palladium in the support is at least about 10 μm and up to about 100 μm, the crystallite size of palladium is between about 40 Å and about 80 Å, and the palladium in the surface layer from the surface of support to a depth of 1 μm is from 10% to 30% based on the total atom number of palladium and other elements. It was confirmed with experiments that such an active component distribution is helpful to improve the catalytic activity, and extend the service life of catalyst. In the meantime, the use of the fluidized bed in the preparation of catalyst can reduce the formation of fine powder of catalyst, increase the content of metallic palladium in catalyst, and bring about good economic benefit.

What is claimed is:

1. A hydrogenation catalyst comprising metallic palladium supported on activated carbon support, wherein the penetration depth of metallic palladium in the support is at least 10 μm and up to 100 μm, the crystallite size of palladium is between 40 Å and 120 Å, and the palladium is present in a surface layer from the surface of the support to a depth of 1 μm in an atom number that is from 5% to 40% of a total atom number of palladium and other elements in the surface layer.

2. A catalyst according to claim 1, wherein the activated carbon support is a granular or shaped activated carbon having a surface area of greater than 600 m²/g and a porosity of from 0.3 to 0.9 ml/g.

3. A catalyst according to claim 2, wherein the activated carbon support is coconut carbon.

4. A catalyst according to claim 1, wherein the penetration depth of metallic palladium in the support is at least 15 μm and up to 100 μm.

5. A catalyst according to claim 1, wherein the crystallite size of palladium is between 40 Å and 80 Å.

6. A catalyst according to claim 1, wherein the atom number of palladium in the surface layer from the surface of support to a depth of 1 μm is from 10% to 30% of the total atom number of palladium and other elements in the surface layer.

7. A catalyst according to claim 1, wherein the amount of metallic palladium supported on the activated carbon support is from 0.1 to 5 wt % based on the total weight of catalyst.

8. A catalyst according to claim 7, wherein the amount of metallic palladium supported on the activated carbon support is from 0.2 to 0.6 wt % based on the total weight of catalyst.

9. A catalyst according to claim 1, further comprising a Group VIII metal selected from a group consisting of ruthenium, platinum, rhodium and iridium.

10. A process for preparing the catalyst according to claim 1, wherein said process comprises placing the activated carbon support between two sieve plates in a fluidized bed, circularly passing upward an aqueous solution through the fluidized bed by using a pump under conditions of effectively fluidizing the activated carbon support, then adding a palladium salt solution under fluidizing state for impregnating the activated carbon support.

11. A process according to claim 10, wherein the palladium salt solution is adsorbed by the activated carbon support at a temperature of 15 to 60° C.

12. A process according to claim 10, wherein the palladium salt solution is treated by pre-adding an oxidant to form a palladium salt oxidation solution.

13. A process according to claim 12, wherein the oxidant is hydrogen peroxide, sodium hypochlorite, or a mixture thereof.

14. A process according to claim 13, wherein the oxidant is a mixture of hydrogen peroxide and sodium hypochlorite, wherein the concentration thereof is 0.01% to 10%, and the mass ratio of hydrogen peroxide to sodium hypochlorite is 1-30:1.

15. A process according to claim 10, wherein the sieve plates in the fluidized bed have an orifice diameter of 1 to 3 mm and an orifice pitch of 2-6 mm.

16. A process according to claim 10, wherein the motion of activated carbon support in solution is controlled by regulating the flow rate of aqueous solution.

17. A process according to claim 16, wherein the flow rate of aqueous solution is from 3.0 to 35.0 L/min.

18. A process for purifying crude terephthalic acid, comprising purifying the crude terephthalic acid by hydrogenation in the presence of the hydrogenation catalyst according to claim 1.

19. The hydrogenation catalyst according to claim 1 prepared by a process comprising placing the activated carbon support between a plurality of sieve plates in a fluidized bed, circularly passing upward an aqueous solution through the fluidized bed under conditions of effectively fluidizing the activated carbon support, then adding a palladium salt solution under fluidizing state for impregnating the activated carbon support.

* * * * *